US010240018B2

(12) United States Patent
Kshirsagar et al.

(10) Patent No.: US 10,240,018 B2
(45) Date of Patent: Mar. 26, 2019

(54) MICROORGANISM CONCENTRATION PROCESS AND DEVICE

(71) Applicant: 3M INNOVATIVE PROPERTIES COMPANY, St. Paul, MN (US)

(72) Inventors: Manjiri T. Kshirsagar, Woodbury, MN (US); Andrew W. Rabins, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 264 days.

(21) Appl. No.: 14/602,603

(22) Filed: Jan. 22, 2015

(65) Prior Publication Data

US 2015/0133574 A1 May 14, 2015

Related U.S. Application Data

(62) Division of application No. 13/257,382, filed as application No. PCT/US2010/028122 on Mar. 22, 2010, now Pat. No. 8,969,011.

(60) Provisional application No. 61/166,266, filed on Apr. 3, 2009.

(51) Int. Cl.
| C08J 9/00 | (2006.01) |
| B01D 61/14 | (2006.01) |
| B01D 63/00 | (2006.01) |
| C12Q 1/24 | (2006.01) |
| C08K 5/54 | (2006.01) |
| C08K 3/105 | (2018.01) |

(52) U.S. Cl.
CPC .......... *C08J 9/0066* (2013.01); *B01D 61/147* (2013.01); *B01D 63/00* (2013.01); *C08J 9/0061* (2013.01); *C12Q 1/24* (2013.01); *C08J 2323/06* (2013.01); *C08J 2423/06* (2013.01); *C08K 3/105* (2018.01); *C08K 5/5406* (2013.01)

(58) Field of Classification Search
CPC ...................................................... C08J 9/24
See application file for complete search history.

(56) References Cited

U.S. PATENT DOCUMENTS

| 4,618,525 | A |  | 10/1986 | Chamberlain |  |
| 5,143,878 | A |  | 9/1992 | Dai |  |
| 5,648,227 | A |  | 7/1997 | Basboll |  |
| 6,038,963 | A |  | 3/2000 | Patterson |  |
| 6,045,913 | A | * | 4/2000 | Castle | B01J 2/16 |
|  |  |  |  |  | 428/403 |
| 6,274,777 | B1 | * | 8/2001 | Gray | C07C 37/70 |
|  |  |  |  |  | 568/790 |
| 7,112,272 | B2 |  | 9/2006 | Hughes |  |
| 7,112,280 | B2 |  | 9/2006 | Hughes |  |
| 7,169,304 | B2 |  | 1/2007 | Hughes |  |
| 7,422,868 | B2 |  | 9/2008 | Fan |  |
| 2003/0140785 | A1 |  | 7/2003 | Koslow |  |
| 2004/0159605 | A1 |  | 8/2004 | Hughes |  |
| 2004/0168974 | A1 | * | 9/2004 | Hughes | B01D 39/1653 |
|  |  |  |  |  | 210/502.1 |
| 2004/0185553 | A9 |  | 9/2004 | Hei |  |
| 2006/0292555 | A1 |  | 12/2006 | Xu |  |
| 2007/0212747 | A1 |  | 9/2007 | Browne |  |
| 2008/0269475 | A1 |  | 10/2008 | Sohling |  |
| 2012/0009563 | A1 |  | 1/2012 | Kshirsagar |  |

FOREIGN PATENT DOCUMENTS

| JP | 62-158485 | 7/1987 |
| JP | 11123076 | 5/1999 |
| JP | 2000/014380 | 1/2000 |
| WO | WO9323142 A1 * | 11/1993 |
| WO | WO 2007/093808 | 8/2007 |
| WO | WO 2009/085357 | 7/2009 |
| WO | WO 2012/078426 | 6/2012 |

OTHER PUBLICATIONS

Machine translation of JP 09087412 by Moriyama, J. et al. Published Mar. 31, 1997.*
Machine translation of JP 2000279500 by Hirukawa, T. et al. Published Oct. 10, 2000.*
Carpenter, et al., "Methods of Sieve Analysis With Particular Reference to Bone Char," Journal of Research of the National Bureau of Standards, vol. 45, No. 4, Oct. 1950, pp. 328-346.
Malvern Instruments, "Dynamic Light Scattering: An Introduction in 30 Minutes," DLS Technical note, MRK656-01, 8 pages.
Krysztafkiewicz, et al., "Amorphous magnesium silicate—synthesis, physicochemical properties and surface morphology," Advanced Powder Technol., vol. 15, No. 5, pp. 549-565, (2004).
Mikli, et al., "Characterization of Powder Particle Morphology," Proc. Estonian Acad. Sci. Eng., vol. 7, No. 1, pp. 22-34, (2001).

* cited by examiner

*Primary Examiner* — Michael M Dollinger
*Assistant Examiner* — Christina H Wales
(74) *Attorney, Agent, or Firm* — Adrian L. Pishko

(57) ABSTRACT

A process for capturing or concentrating microorganisms for detection or assay comprises (a) providing a concentration device comprising a sintered porous polymer matrix comprising at least one concentration agent that comprises an amorphous metal silicate and that has a surface composition having a metal atom to silicon atom ratio of less than or equal to 0.5, as determined by X-ray photoelectron spectroscopy (XPS); (b) providing a sample comprising at least one microorganism strain; and (c) contacting the concentration device with the sample such that at least a portion of the at least one microorganism strain is bound to or captured by the concentration device.

20 Claims, No Drawings

MICROORGANISM CONCENTRATION PROCESS AND DEVICE

CROSS REFERENCE TO RELATED APPLICATIONS

This application is a divisional application of U.S. application Ser. No. 13/257,382, filed Sep. 19, 2011 which is a national stage filing under 35 U.S.C. 371 of PCT/US2010/028122, filed Mar. 22, 2010, which claims priority to U.S. Provisional Application No. 61/166,266, filed Apr. 3, 2009, the disclosures of which are incorporated by reference in their entirety herein.

FIELD

This invention relates to processes for capturing or concentrating microorganisms such that they remain viable for detection or assay. In other aspects, this invention also relates to concentration devices (and diagnostic kits comprising the devices) for use in carrying out such processes and to methods for device preparation.

BACKGROUND

Food-borne illnesses and hospital-acquired infections resulting from microorganism contamination are a concern in numerous locations all over the world. Thus, it is often desirable or necessary to assay for the presence of bacteria or other microorganisms in various clinical, food, environmental, or other samples, in order to determine the identity and/or the quantity of the microorganisms present.

Bacterial DNA or bacterial RNA, for example, can be assayed to assess the presence or absence of a particular bacterial species even in the presence of other bacterial species. The ability to detect the presence of a particular bacterium, however, depends, at least in part, on the concentration of the bacterium in the sample being analyzed. Bacterial samples can be plated or cultured to increase the numbers of the bacteria in the sample to ensure an adequate level for detection, but the culturing step often requires substantial time and therefore can significantly delay the assessment results.

Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or non-magnetic particles). Such methods, however, have tended to be expensive and still somewhat slower than desired for at least some diagnostic applications.

Concentration methods that are not strain-specific have also been used (for example, to obtain a more general assessment of the microorganisms present in a sample). After concentration of a mixed population of microorganisms, the presence of particular strains can be determined, if desired, by using strain-specific probes.

Non-specific concentration or capture of microorganisms has been achieved through methods based upon carbohydrate and lectin protein interactions. Chitosan-coated supports have been used as non-specific capture devices, and substances (for example, carbohydrates, vitamins, iron-chelating compounds, and siderophores) that serve as nutrients for microorganisms have also been described as being useful as ligands to provide non-specific capture of microorganisms.

Various inorganic materials (for example, hydroxyapatite and metal hydroxides) have been used to non-specifically bind and concentrate bacteria. Physical concentration methods (for example, filtration, chromatography, centrifugation, and gravitational settling) have also been utilized for non-specific capture, with and/or without the use of inorganic binding agents. Such non-specific concentration methods have varied in speed (at least some food testing procedures still requiring at least overnight incubation as a primary cultural enrichment step), cost (at least some requiring expensive equipment, materials, and/or trained technicians), sample requirements (for example, sample nature and/or volume limitations), space requirements, ease of use (at least some requiring complicated multi-step processes), suitability for on-site use, and/or effectiveness.

SUMMARY

Thus, we recognize that there is an urgent need for processes for rapidly detecting pathogenic microorganisms. Such processes will preferably be not only rapid but also low in cost, simple (involving no complex equipment or procedures), and/or effective under a variety of conditions (for example, with varying types of sample matrices and/or pathogenic microorganisms, varying microorganism loads, and varying sample volumes).

Briefly, in one aspect, this invention provides a process for non-specifically concentrating the strains of microorganisms (for example, strains of bacteria, fungi, yeasts, protozoans, viruses (including both non-enveloped and enveloped viruses), and bacterial endospores) present in a sample, such that the microorganisms remain viable for the purpose of detection or assay of one or more of the strains. The process comprises (a) providing a concentration device comprising a sintered porous polymer matrix comprising at least one concentration agent that comprises an amorphous metal silicate and that has a surface composition having a metal atom to silicon atom ratio of less than or equal to 0.5, as determined by X-ray photoelectron spectroscopy (XPS); (b) providing a sample (preferably, in the form of a fluid) comprising at least one microorganism strain; and (c) contacting the concentration device with the sample (preferably, by passing the sample through the concentration device) such that at least a portion of the at least one microorganism strain is bound to or captured by the concentration device.

Preferably, the process further comprises detecting the presence of at least one bound microorganism strain (for example, by culture-based, microscopy/imaging, genetic, luminescence-based, or immunologic detection methods). The process can optionally further comprise separating the concentration device from the sample and/or culturally enriching at least one bound microorganism strain (for example, by incubating the separated concentration device in a general or microorganism-specific culture medium, depending upon whether general or selective microorganism enrichment is desired) and/or isolating or separating captured microorganisms (or one or more components thereof) from the concentration device after sample contacting (for example, by passing an elution agent or a lysis agent through the concentration device).

The process of the invention does not target a specific microorganism strain. Rather, it has been discovered that a concentration device comprising certain relatively inexpensive, inorganic materials in a sintered porous polymer matrix can be surprisingly effective in capturing a variety of microorganisms (and surprisingly effective in isolating or separating the captured microorganisms via elution, relative to corresponding devices without the inorganic material). Such devices can be used to concentrate the microorganism strains present in a sample (for example, a food sample) in a non-strain-specific manner, so that one or more of the microorganism strains (preferably, one or more strains of bacteria) can be more easily and rapidly assayed.

The process of the invention is relatively simple and low in cost (requiring no complex equipment or expensive strain-specific materials) and can be relatively fast (preferred embodiments capturing at least about 70 percent (more preferably, at least about 80 percent; most preferably, at least about 90 percent) of the microorganisms present in a relatively homogeneous fluid sample in less than about 30 minutes, relative to a corresponding control sample having no contact with the concentration device). In addition, the process can be effective with a variety of microorganisms (including pathogens such as both gram positive and gram negative bacteria) and with a variety of samples (different sample matrices and, unlike at least some prior art methods, even samples having low microorganism content and/or large volumes). Thus, at least some embodiments of the process of the invention can meet the above-cited urgent need for low-cost, simple processes for rapidly detecting pathogenic microorganisms under a variety of conditions.

The process of the invention can be especially advantageous for concentrating the microorganisms in food samples (for example, particulate-containing food samples, especially those comprising relatively coarse particulates), as the concentration device used in the process can exhibit at least somewhat greater resistance to clogging than at least some filtration devices such as absolute micron filters. This can facilitate more complete sample processing (which is essential to eliminating false negative assays in food testing) and the handling of relatively large volume samples (for example, under field conditions).

In another aspect, the invention also provides a concentration device comprising a sintered porous polymer matrix comprising at least one concentration agent that comprises an amorphous metal silicate and that has a surface composition having a metal atom to silicon atom ratio of less than or equal to 0.5, as determined by X-ray photoelectron spectroscopy (XPS). The invention also provides a diagnostic kit for use in carrying out the concentration process of the invention, the kit comprising (a) at least one said concentration device of the invention; and (b) at least one testing container or testing reagent for use in carrying out the above-described concentration process.

In yet another aspect, the invention provides a process for preparing a concentration device comprising (a) providing a mixture comprising (1) at least one particulate, sinterable polymer (preferably, in the form of a powder) and (2) at least one particulate concentration agent that comprises an amorphous metal silicate and that has a surface composition having a metal atom to silicon atom ratio of less than or equal to 0.5, as determined by X-ray photoelectron spectroscopy (XPS); and (b) heating the mixture to a temperature sufficient to sinter the polymer, so as to form a sintered porous polymer matrix comprising the particulate concentration agent.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range.

Definitions

As used in this patent application:

"concentration agent" means a composition for concentrating microorganisms;

"detection" means the identification of at least a component of a microorganism, which thereby determines that the microorganism is present;

"genetic detection" means the identification of a component of genetic material such as DNA or RNA that is derived from a target microorganism;

"immunologic detection" means the identification of an antigenic material such as a protein or a proteoglycan that is derived from a target microorganism;

"microorganism" means any cell or particle having genetic material suitable for analysis or detection (including, for example, bacteria, yeasts, viruses, and bacterial endospores);

"microorganism strain" means a particular type of microorganism that is distinguishable through a detection method (for example, microorganisms of different genera, of different species within a genera, or of different isolates within a species);

"sample" means a substance or material that is collected (for example, to be analyzed);

"sample matrix" means the components of a sample other than microorganisms;

"sinter" (in reference to a mass of polymer particles) means to cause inter-particle binding or adhesion of at least some of the polymer particles through application of heat, without causing complete particle melting (for example, by heating the mass of polymer particles to a temperature between the glass transition temperature and the melting point of the polymer to effect particle softening);

"sinterable" (in reference to a polymer) means a polymer that can be sintered;

"sintered" (in reference to a matrix) means formed by sintering;

"target microorganism" means any microorganism that is desired to be detected;

"through pore" (in reference to a porous matrix) means a pore that comprises a passageway or channel (with separate inlet and outlet) through the matrix; and "tortuous path matrix" means a porous matrix having at least one tortuous through pore.

Concentration Agent

Concentration agents suitable for use in carrying out the process of the invention include those that comprise a metal silicate and that have a surface composition having a metal atom to silicon atom ratio of less than or equal to about 0.5 (preferably, less than or equal to about 0.4; more preferably, less than or equal to about 0.3; most preferably, less than or equal to about 0.2), as determined by X-ray photoelectron spectroscopy (XPS). Preferably, the surface composition also comprises at least about 10 average atomic percent carbon (more preferably, at least about 12 average atomic percent carbon; most preferably, at least about 14 average atomic percent carbon), as determined by X-ray photoelectron spectroscopy (XPS). XPS is a technique that can determine the elemental composition of the outermost approximately 3 to 10 nanometers (nm) of a sample surface and that is sensitive to all elements in the periodic table except hydrogen and helium. XPS is a quantitative technique with detection limits for most elements in the 0.1 to 1 atomic percent concentration range. Preferred surface composition assessment conditions for XPS can include a take-off angle of 90 degrees measured with respect to the sample surface with a solid angle of acceptance of ±10 degrees.

Concentration or capture using such concentration agents is generally not specific to any particular strain, species, or type of microorganism and therefore provides for the concentration of a general population of microorganisms in a sample. Specific strains of microorganisms can then be detected from among the captured microorganism population using any known detection method with strain-specific probes. Thus, the concentration agents can be used for the detection of microbial contaminants or pathogens (particularly food-borne pathogens such as bacteria) in clinical, food, environmental, or other samples.

When dispersed or suspended in water systems, inorganic materials such as metal silicates exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). The concentration agents used in carrying out the process of the invention have zeta potentials that are more negative than that of, for example, a common metal silicate such as ordinary talc. Yet the concentration agents can be surprisingly more effective than talc in concentrating microorganisms such as bacteria, the surfaces of which generally tend to be negatively charged. Preferably, the concentration agents have a negative zeta potential at a pH of about 7 (more preferably, a Smoluchowski zeta potential in the range of about −9 millivolts to about −25 millivolts at a pH of about 7; even more preferably, a Smoluchowski zeta potential in the range of about −10 millivolts to about −20 millivolts at a pH of about 7; most preferably, a Smoluchowski zeta potential in the range of about −11 millivolts to about −15 millivolts at a pH of about 7).

Useful metal silicates include amorphous silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form (more preferably, amorphous, spheroidized metal silicates; most preferably, amorphous, spheroidized magnesium silicate). Metal silicates are known and can be chemically synthesized by known methods or obtained through the mining and processing of raw ores that are naturally-occurring.

Amorphous, at least partially fused particulate forms of metal silicates can be prepared by any of the known methods of melting or softening relatively small feed particles (for example, average particle sizes up to about 25 microns) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle), the description of which is incorporated herein by reference). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, as 3M™ Cosmetic Microspheres CM-111, available from 3M Company, St. Paul, Minn.).

In addition to amorphous metal silicates, the concentration agents can further comprise other materials including oxides of metals (for example, iron or titanium), crystalline metal silicates, other crystalline materials, and the like, provided that the concentration agents have the above-described surface compositions. The concentration agents, however, preferably contain essentially no crystalline silica.

In carrying out the process of the invention, the concentration agents can be used in essentially any particulate form (preferably, a relatively dry or volatiles-free form) that is amenable to blending with particulate polymer to form the concentration device used in the process. For example, the concentration agents can be used in powder form or can be applied to a particulate support such as beads or the like.

Preferably, the concentration agents are used in the form of a powder. Useful powders include those that comprise microparticles (preferably, microparticles having a particle size in the range of about 1 micrometer (more preferably, about 2 micrometers) to about 100 micrometers (more preferably, about 50 micrometers; even more preferably, about 25 micrometers; most preferably, about 15 micrometers; where any lower limit can be paired with any upper limit of the range as referenced above).

Concentration Device

Concentration devices suitable for use in carrying out the process of the invention include those that comprise a sintered porous polymer matrix comprising at least one of the above-described concentration agents. Such concentration devices can be prepared, for example, by mixing or blending at least one particulate, sinterable polymer (preferably, in the form of a powder) and at least one particulate concentration agent, and then heating the resulting mixture to a temperature sufficient to sinter the polymer. This process, as well as other known or hereafter-developed sintering processes, can be used to provide, upon cooling, a sintered porous polymer matrix comprising the particulate concentration agent.

For example, sintering can cause the polymer particles to soften at their points of contact, and subsequent cooling can then cause fusion of the particles. A solidified or self-supporting, porous polymer body comprising particulate concentration agent can result (for example, with the concentration agent being embedded in or on the surface of the polymer body). This can provide a concentration device having a relatively complex pore structure (preferably, a concentration device comprising a tortuous path matrix) and relatively good mechanical strength.

Polymers suitable for use in preparing the concentration device include sinterable polymers and combinations thereof. Preferred sinterable polymers include thermoplastic polymers and combinations thereof. More preferably, the thermoplastic polymers can be selected so as to have relatively high viscosities and relatively low melt flow rates. This can facilitate particle shape retention during the sintering process.

Useful sinterable polymers include polyolefins (including olefin homopolymers and copolymers, as well as copolymers of olefins and other vinyl monomers), polysulfones, polyethersulfones, polyphenylene sulfide, and the like, and combinations thereof. Representative examples of useful polymers include ethylene vinyl acetate (EVA) polymers, ethylene methyl acrylate (EMA) polymers, polyethylenes (including, for example, low density polyethylene (LDPE), linear low density polyethylene (LLDPE), high density polyethylene (HDPE), and ultra-high molecular weight polyethylene (UHMWPE)), polypropylenes, ethylene-propylene rubbers, ethylene-propylene-diene rubbers, polystyrene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, poly(vinyl acetate), poly(vinylidene chloride), poly(vinylidene fluoride), poly(tetrafluoroethylene), and the like, and combinations thereof.

Preferred polymers include olefin homopolymers and copolymers (especially, polyethylenes, polypropylenes, ethylene vinyl acetate polymers, and combinations thereof). More preferred polymers include olefin homopolymers and combinations thereof (even more preferably, polyethylenes and combinations thereof most preferably, ultra-high molecular weight polyethylenes (UHMWPE) and combinations thereof). Useful ultra-high molecular weight polyethylenes include those having a molecular weight of at least about 750,000 (preferably, at least about 1,000,000; more preferably, at least about 2,000,000; most preferably, at least about 3,000,000).

A wide range of polymer particle sizes can be utilized, depending upon the pore (for example, hole, depression, or, preferably, channel) sizes desired in the sintered porous polymer matrix. Finer particles can provide finer pore sizes in the sintered matrix. Generally, the polymer particles can be microparticles (for example, ranging in size or diameter from about 1 micrometer to about 800 micrometers; preferably, from about 5 micrometers to about 300 micrometers; more preferably, from about 5 micrometers to about 200 micrometers; most preferably, from about 10 micrometers to about 100 or 200 micrometers), so as to provide pore sizes on the order of micrometers or less. Varying average (mean) and/or median particle sizes can be utilized (for example, average particle sizes of about 30 micrometers to about 70 micrometers can be useful). If desired, the porosity of the sintered matrix can also be varied or controlled by using blends of higher and lower melt flow rate polymers.

The polymer particles and the particulate concentration agent (and any optional additives, such as wetting agents or surfactants) can be combined and mechanically blended (for example, using commercial mixing equipment) to form a mixture (preferably, a homogeneous mixture). Generally, the particulate concentration agent can be present in the mixture at a concentration of up to about 90 weight percent (preferably, about 5 to about 85 weight percent; more preferably, about 10 to about 80 weight percent; most preferably, about 15 to about 75 weight percent), based upon the total weight of all particles in the mixture. Conventional additives (for example, wetting agents, surfactants, or the like) can be included in the mixture in small amounts (for example, up to about 5 weight percent), if desired.

The resulting mixture can be placed in a mold or other suitable container or substrate. Useful molds can be made of carbon steel, stainless steel, brass, aluminum, or the like, and can have a single cavity or multiple cavities. The cavities can be of essentially any desired shape, provided that their sintered contents can be removed from the mold after processing is completed. Preferably, mold filling can be assisted by using commercial powder handling and/or vibratory equipment.

Thermal processing can be carried out by introducing heat to the mold (for example, through electrical resistance heating, electrical induction heating, or steam heating). The mold can be heated to a temperature sufficient to sinter the polymer (for example, by heating to a temperature slightly below the melting point of the polymer). Sintering methods are known and can be selected according to the nature and/or form of the polymer(s) utilized. Optionally, pressure can be applied to the mixture during the heating process. After thermal processing, the mold can be allowed to cool to ambient temperature (for example, a temperature of about 23° C.) naturally or through use of essentially any convenient cooling method or device.

A preferred concentration device can be prepared by using the polymer particles and processing methods described in U.S. Pat. Nos. 7,112,272, 7,112,280, and 7,169,304 (Hughes et al.), the descriptions of which particles and methods are incorporated herein by reference. Two different types of ultra-high molecular weight polyethylene (UHMWPE) particles can be blended together, one being "popcorn-shaped" (having surface convolutions) and the other being substantially spherical. Preferred "popcorn-shaped" and spherical UHMWPEs are available from Ticona (a division of Celanese, headquartered in Frankfurt, Germany) as PMX CF-1 (having a bulk density of 0.25-0.30 g/cubic centimeter and an average diameter of about 30 to 40 micrometers, with a range from about 10 micrometers to about 100 micrometers) and PMX CF-2 (having a bulk density of 0.40-0.48 g/cubic centimeter and an average diameter of about 55 to 65 micrometers, with a range from about 10 micrometers to about 180 micrometers), respectively. UHMWPEs from other manufacturers having comparable morphologies, bulk densities, and particle sizes and having molecular weights in the range of about 750,000 to about 3,000,000 can also be utilized. The two types of UHMWPE particles can be selected to be of the same or different molecular weight(s) (preferably, both have the same molecular weight within the stated range; more preferably, both have molecular weights of about 3,000,000).

The two types of UHMWPE particles can be combined in varying relative amounts (for example, equal amounts) and then further combined with concentration agent in the ratios described above. Either type of UHMWPE can be used in lesser amount than the other, or can even be omitted from the mixture, depending upon the desired characteristics of the concentration device.

The selected particles can be blended together to form a mixture that is preferably homogeneous. For example, a ribbon blender or the like can be used. The resulting mixture can then be placed in a mold cavity while preferably being simultaneously vibrated using essentially any standard mechanical vibrator. At the end of the filling and vibration cycle, the mold can be heated to a temperature that is sufficient to sinter the polymer(s) (generally, a temperature in the range of about 225° F. to about 375° F. or higher, depending upon the molecular weight(s) of the polymer(s)).

Upon cooling, a self-supporting, sintered porous polymer matrix can be obtained. The matrix can exhibit a complex internal structure comprising interconnected, multi-directional through pores of varying diameters and can thus comprise a preferred tortuous path matrix for use as a concentration device in the concentration process of the invention. If desired, the concentration device can further comprise one or more other components such as, for example, one or more pre-filters (for example, to remove relatively large food particles from a sample prior to passage of the sample through the porous matrix), a manifold for applying a pressure differential across the device (for example, to aid in passing a sample through the porous matrix), and/or an external housing (for example, a disposable cartridge to contain and/or protect the porous matrix).

Sample

The process of the invention can be applied to a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), a laboratory, or an area that has been potentially subjected to bioterrorism. Food processing, handling, and preparation area samples are preferred, as these are often of particular concern in regard to food supply contamination by bacterial pathogens.

Samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be used directly or can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is a fluid (for example, a liquid, a gas, or a dispersion or suspension of solid or liquid in liquid or gas).

Examples of samples that can be used in carrying out the process of the invention include foods (for example, fresh produce or ready-to-eat lunch or "deli" meats), beverages (for example, juices or carbonated beverages), potable water, and biological fluids (for example, whole blood or a component thereof such as plasma, a platelet-enriched blood fraction, a platelet concentrate, or packed red blood cells; cell preparations (for example, dispersed tissue, bone marrow aspirates, or vertebral body bone marrow); cell suspensions; urine, saliva, and other body fluids; bone marrow; lung fluid; cerebral fluid; wound exudate; wound biopsy samples; ocular fluid; spinal fluid; and the like), as well as lysed preparations, such as cell lysates, which can be formed using known procedures such as the use of lysing buffers, and the like. Preferred samples include foods, beverages, potable water, biological fluids, and combinations thereof (with foods, beverages, potable water, and combinations thereof being more preferred).

Sample volume can vary, depending upon the particular application. For example, when the process of the invention is used for a diagnostic or research application, the volume of the sample can typically be in the microliter range (for example, 10 microliters or greater). When the process is used for a food pathogen testing assay or for potable water safety testing, the volume of the sample can typically be in the milliliter to liter range (for example, 100 milliliters to 3 liters). In an industrial application, such as bioprocessing or pharmaceutical formulation, the volume can be tens of thousands of liters.

The process of the invention can isolate microorganisms from a sample in a concentrated state and can also allow the isolation of microorganisms from sample matrix components that can inhibit detection procedures that are to be used. In all of these cases, the process of the invention can be used in addition to, or in replacement of, other methods of microorganism concentration. Thus, optionally, cultures can be grown from samples either before or after carrying out the process of the invention, if additional concentration is desired. Such cultural enrichment can be general or primary (so as to enrich the concentrations of most or essentially all microorganisms) or can be specific or selective (so as to enrich the concentration(s) of one or more selected microorganisms only).

Contacting

The process of the invention can be carried out by any of various known or hereafter-developed methods of providing contact between two materials. For example, the concentration device can be added to the sample, or the sample can be added to the concentration device. The concentration device can be immersed in a sample, a sample can be poured onto the concentration device, a sample can be poured into a tube or well containing the concentration device, or, preferably, a sample can be passed over or through (preferably, through) the concentration device (or vice versa). Preferably, the contacting is carried out in a manner such that the sample passes through at least one pore of the sintered porous polymer matrix (preferably, through at least one through pore).

The concentration device and the sample can be combined (using any order of addition) in any of a variety of containers or holders (optionally, a capped, closed, or sealed container; preferably, a column, a syringe barrel, or another holder designed to contain the device with essentially no sample leakage). Suitable containers for use in carrying out the process of the invention will be determined by the particular sample and can vary widely in size and nature. For example, the container can be small, such as a 10 microliter container (for example, a test tube or syringe) or larger, such as a 100 milliliter to 3 liter container (for example, an Erlenmeyer flask or an annular cylindrical container).

The container, the concentration device, and any other apparatus or additives that contact the sample directly can be sterilized (for example, by controlled heat, ethylene oxide gas, or radiation) prior to use, in order to reduce or prevent any contamination of the sample that might cause detection errors. The amount of concentration agent in the concentration device that is sufficient to capture or concentrate the microorganisms of a particular sample for successful detection will vary (depending upon, for example, the nature and form of the concentration agent and device and the volume of the sample) and can be readily determined by one skilled in the art.

Contacting can be carried out for a desired period (for example, for sample volumes of about 100 milliliters or less, up to about 60 minutes of contacting can be useful; preferably, about 15 seconds to about 10 minutes or longer; more preferably, about 15 seconds to about 5 minutes; most preferably, about 15 seconds to about 2 minutes). Contact can be enhanced by mixing (for example, by stirring, by shaking, or by application of a pressure differential across the device to facilitate passage of a sample through its porous matrix) and/or by incubation (for example, at ambient temperature), which are optional but can be preferred, in order to increase microorganism contact with the concentration device.

Preferably, contacting can be effected by passing a sample at least once (preferably, only once) through the concentration device (for example, by pumping). Essentially any type of pump (for example, a peristaltic pump) or other equipment for establishing a pressure differential across the device (for example, a syringe or plunger) can be utilized. Sample flow rates through the device of up to about 100 milliliters per minute or more can be effective. Preferably, flow rates of about 10-20 milliliters per minute can be utilized.

A preferred contacting method includes such passing of a sample through the concentration device (for example, by pumping) and then incubating (for example, for about 3 hours to about 24 hours; preferably, about 4 hours to about 20 hours) a microorganism-containing sample (preferably, a fluid) with the concentration device (for example, in one of the above-described containers). If desired, one or more additives (for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, Triton™ X-100 nonionic surfactant available from Union Carbide Chemicals and Plastics, Houston, Tex.), mechanical abrasion/elution agents (for example, glass beads), and the like) can be included in the combination of concentration device and sample during contacting.

The process of the invention can optionally further comprise separating the resulting microorganism-bound concentration device and the sample. Separation can be carried out by numerous methods that are well-known in the art (for example, by pumping, decanting, or siphoning a fluid sample, so as to leave the microorganism-bound concentration device in the container or holder utilized in carrying out the process). It can also be possible to isolate or separate captured microorganisms (or one or more components thereof) from the concentration device after sample contacting (for example, by passing an elution agent or a lysis agent over or through the concentration device).

The process of the invention can be carried out manually (for example, in a batch-wise manner) or can be automated (for example, to enable continuous or semi-continuous processing).

Detection

A variety of microorganisms can be concentrated and, optionally but preferably, detected by using the process of the invention, including, for example, bacteria, fungi, yeasts, protozoans, viruses (including both non-enveloped and enveloped viruses), bacterial endospores (for example, *Bacillus* (including *Bacillus anthracis, Bacillus cereus*, and *Bacillus subtilis*) and *Clostridium* (including *Clostridium botulinum, Clostridium difficile*, and *Clostridium perfringens*)), and the like, and combinations thereof (preferably, bacteria, yeasts, viruses, bacterial endospores, fungi, and combinations thereof; more preferably, bacteria, yeasts, viruses, bacterial endospores, and combinations thereof; even more preferably, bacteria, viruses, bacterial endospores, and combinations thereof; most preferably, gram-negative bacteria, gram-positive bacteria, non-enveloped viruses (for example, norovirus, poliovirus, hepatitis A virus, rhinovirus, and combinations thereof), bacterial endospores, and combinations thereof). The process has utility in the detection of pathogens, which can be important for food safety or for medical, environmental, or anti-terrorism reasons. The process can be particularly useful in the detection of pathogenic bacteria (for example, both gram negative and gram positive bacteria), as well as various yeasts, molds, and mycoplasmas (and combinations of any of these).

Genera of target microorganisms to be detected include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida*, and the like, and combinations thereof. Samples can contain a plurality of microorganism strains, and any one strain can be detected independently of any other strain. Specific microorganism strains that can be targets for detection include *Escherichia coli, Yersinia enterocolitica, Yersinia pseudotuberculosis, Vibrio cholerae, Vibrio parahaemolyticus, Vibrio vulnificus, Listeria monocytogenes* (for which *Listeria innocua* is a surrogate), *Staphylococcus aureus, Salmonella enterica, Saccharomyces cerevisiae, Candida albicans*, Staphylococcal enterotoxin ssp, *Bacillus cereus, Bacillus anthracis, Bacillus atrophaeus, Bacillus subtilis, Clostridium perfringens, Clostridium botulinum, Clostridium difficile, Enterobacter sakazakii, Pseudomonas aeruginosa*, and the like, and combinations thereof (preferably, *Staphylococcus aureus, Salmonella enterica, Saccharomyces cerevisiae, Bacillus atrophaeus, Bacillus subtilis, Escherichia coli*, human-infecting non-enveloped enteric viruses for which *Escherichia coli* bacteriophage is a surrogate, and combinations thereof).

Microorganisms that have been captured or bound (for example, by adsorption or by sieving) by the concentration device can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components, slicing or otherwise breaking up the sintered porous polymer matrix of the concentration device, staining, or the like.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adenosine triphosphate (ATP) detection methods including those described in U.S. Pat. No. 7,422,868 (Fan et al.), the descriptions of which are incorporated herein by reference. Other luminescence-based detection methods can also be utilized.

Since the process of the invention is non-strain specific, it provides a general capture system that allows for multiple microorganism strains to be targeted for assay in the same sample. For example, in assaying for contamination of food samples, it can be desired to test for *Listeria monocytogenes, Escherichia coli*, and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

Diagnostic Kit

A diagnostic kit for use in carrying out the concentration process of the invention comprises (a) at least one above-described concentration device; and (b) at least one testing container or testing reagent (preferably, a sterile testing container or testing reagent) for use in carrying out the concentration process of the invention. Preferably, the diagnostic kit further comprises instructions for carrying out the process.

Useful testing containers or holders include those described above and can be used, for example, for contacting, for incubation, for collection of eluate, or for other desired process steps. Useful testing reagents include microorganism culture or growth media, lysis agents, elution agents, buffers, luminescence detection assay components (for example, luminometer, lysis reagents, luciferase enzyme, enzyme substrate, reaction buffers, and the like), genetic detection assay components, and the like, and combinations thereof. A preferred lysis agent is a lytic enzyme or chemical supplied in a buffer, and preferred genetic detection assay components include one or more primers specific for a target microorganism. The kit can optionally further comprise sterile forceps or the like.

EXAMPLES

Objects and advantages of this invention are further illustrated by the following examples, but the particular materials and amounts thereof recited in these examples, as well as other conditions and details, should not be construed to unduly limit this invention. All microorganism cultures were purchased from The American Type Culture Collection (ATCC; Manassas, Va.).

Concentration Agents

Crystalline magnesium silicate concentration agent (hereinafter, Talc) was purchased from Mallinckrodt Baker, Inc. (Phillipsburg, N.J.).

Amorphous, spheroidized magnesium silicate concentration agent (hereinafter, AS-Talc) was obtained as 3M™ Cosmetic Microspheres CM-111 (shaped as solid spheres; particle density of 2.3 g/cubic centimeter; surface area of 3.3 $m^2/g$; particle size: 90 percent less than about 11 microns, 50 percent less than about 5 microns, 10 percent less than about 2 microns; available from 3M Company, St. Paul, Minn.).

Zeta Potential Measurements

Zeta potentials of aqueous dispersions of the Talc and AS-Talc concentration agents (5.75 weight percent Talc and 5.8 weight percent AS-Talc, respectively, in 18 mega ohms deionized water obtained by using a Milli-Q™ Elix 10™ Synthesis A10 deionization system from Millipore Corporation, Bedford, Mass.) were measured as a function of added hydrochloric acid (pH) using a Colloidal Dynamics Acoustosizer II™ multi-frequency electroacoustic spectral analyzer (Colloidal Dynamics, Warwick, R.I.) equipped with a TM200 automatic titration module, pH electrode, and in-line conductivity cell. Measurements were made using polar calibration and polar sample settings with the following general parameters:

Starting Volume: 170 mL of dispersion
Titration Volume: 5 to 10 mL at finish; 20 steps for each titration
Titrant: 1.0 N hydrochloric acid in water (J. T. Baker, Phillipsburg, N.J.)
Stir Rate: 300 revolutions per minute (rpm)
Pump Rate: 400 mL per minute
Mixing Delay: 120 seconds with stirring after acid addition before measurement At a pH of about 7, the AS-Talc exhibited a Smoluchowski zeta potential of about −12 mV, and the Talc exhibited a Smoluchowski zeta potential of about −8 mV.

Surface Composition Analysis

The surface compositions of samples of the Talc and AS-Talc concentration agents were analyzed by X-ray photoelectron spectroscopy (XPS; also known as ESCA). Samples of the powders were pressed onto double-sided, pressure sensitive adhesive tapes on aluminum foil. Excess powder was removed from each sample surface by blowing with compressed nitrogen gas.

Spectral data was acquired using a Kratos AXIS Ultra™ DLD spectrometer (Kratos Analytical, Manchester, England) having a monochromatic Al-$K_\alpha$ X-ray excitation source (1487 eV) and a hemispherical electron energy analyzer operated in a constant pass energy mode. The emitted photoelectrons were detected at a take-off angle of 90 degrees measured with respect to the sample surface with a solid angle of acceptance of ±10 degrees. A low-energy electron flood gun was used to minimize surface charging. Measurements were made using a 140 Watt power to anode and $2 \times 10^{-8}$ Torr chamber pressure.

An area of the surface of each concentration agent sample measuring about 300 micrometers by about 700 micrometers was analyzed for each data point. Three areas on each sample were analyzed and averaged to obtain the reported average atomic percent values. Data processing was carried out using standard Vision2™ software (Kratos Analytical, Manchester, England). Results (elements present at a detectable level by XPS on the surface of the concentration agents) are shown in Table A below:

TABLE A

| Concentration Agent | Magnesium (Average Atomic Percent) | Silicon (Average Atomic Percent) | Ratio of Magnesium to Silicon | Carbon (Average Atomic Percent) | Oxygen (Average Atomic Percent) |
|---|---|---|---|---|---|
| Talc | 17 | 26 | 0.65 | 6.9 | 50 |
| AS-Talc | 6.5 | 32 | 0.20 | 14 | 47 |

Concentration Agent Screening: Microorganism Concentration Test Method

An isolated microorganism colony was inoculated into 5 mL BBL™ Trypticase™ Soy Broth (Becton Dickinson, Sparks, Md.) and incubated at 37° C. for 18-20 hours. This overnight culture at ~$10^9$ colony forming units per mL was diluted in adsorption buffer (containing 5 mM KCl, 1 mM $CaCl_2$, 0.1 mM $MgCl_2$, and 1 mM $K_2HPO_4$) at pH 7.2 to obtain $10^3$ microorganisms per mL dilution. A 1.1 mL volume of the microorganism dilution was added to separate, labeled sterile 5 mL polypropylene tubes (BD Falcon™, Becton Dickinson, Franklin Lakes, N.J.) containing 10 mg of concentration agent, each of which was capped and mixed on a Thermolyne Maximix Plus™ vortex mixer (Barnstead International, Iowa). Each capped tube was incubated at room temperature (25° C.) for 15 minutes on a Thermolyne Vari Mix™ shaker platform (Barnstead International, Iowa). After the incubation, each tube was allowed to stand on the lab bench for 10 minutes to settle the concentration agent. Control sample tubes containing 1.1 mL of the microorganism dilution without concentration agent were treated in the same manner. The resulting settled concentration agent and/or supernatant (and the control samples) were then used for analysis.

The settled concentration agent was re-suspended in 1 mL sterile Butterfield's Buffer solution (pH 7.2±0.2; monobasic potassium phosphate buffer solution; VWR Catalog Number 83008-093, VWR, West Chester, Pa.) and plated on 3M™ Petrifilm™ Aerobic Count Plates culture medium (dry, rehydratable; 3M Company, St. Paul., MN) according to the manufacturer's instructions. Aerobic count was quantified using a 3M™ Petrifilm™ Plate Reader (3M Company, St. Paul., MN). Results were calculated using the following formula:

Percent CFU/mL in Re-suspended Concentration Agent=(number of colonies from plated re-suspended concentration agent)/(number of colonies from plated untreated control sample)×100 (where CFU=Colony Forming Unit, which is a unit of live or viable microorganisms).

Results were then reported in terms of percent capture of microorganisms by the concentration agent using the formula below:

Capture Efficiency or Percent Capture=Percent CFU/mL in Re-suspended Concentration Agent For comparison purposes, in at least some cases 1 mL of the supernatant was removed and plated undiluted or diluted 1:10 in Butterfield's Buffer solution and plated onto 3M™ Petrifilm™ Aerobic Count Plates culture medium. Aerobic count was quantified using a 3M™ Petrifilm™ Plate Reader (3M Company, St. Paul., MN). Results were calculated using the following formula:

Percent CFU/mL in Supernatant=(number of colonies from plated supernatant)/(number of colonies from plated untreated control sample)×100

(where CFU=Colony Forming Unit, which is a unit of live or viable microorganisms). When the microorganism colonies and the concentration agent were similar in color (providing little contrast for the plate reader), results were based upon the supernatant and were then reported in terms of percent capture of microorganisms by the concentration agent using the formula below:

Capture Efficiency or Percent Capture=100−Percent CFU/mL in Supernatant

Concentration Agent Screenings 1 and 2 and Comparative Screenings 1 and 2

Using the above-described microorganism concentration test method, 10 mg amorphous, spheroidized magnesium silicate (prepared as described above; hereinafter, AS-Talc) and crystalline (non-spheroidized) magnesium silicate (hereinafter, Talc) were tested separately for bacterial concentration against target microorganisms, the gram-negative bacterium *Salmonella enterica* subsp.*enterica serovar Typhimurium* (ATCC 35987) and the gram-positive bacterium *Staphylococcus aureus* (ATCC 6538). The results are shown in Table 1 below (standard deviation for all samples less than 10 percent).

TABLE 1

| Screening No. | Microorganism | Concentration Agent | Percent Capture |
|---|---|---|---|
| C-1 | *Staphylococcus* | Talc | 58 |
| 1 | *Staphylococcus* | AS-Talc | 99 |
| C-2 | *Salmonella* | Talc | 69 |
| 2 | *Salmonella* | AS-Talc | 92 |

Concentration Agent Screenings 3-5 and Comparative Screenings 3-5

Using the above-described microorganism concentration test method, different weights per unit volume of AS-Talc and Talc were tested separately for bacterial concentration of the target microorganism, *Salmonella enterica* subsp.*enterica serovar Typhimurium* (ATCC 35987). The results are shown in Table 2 below (standard deviation for all samples less than 10 percent).

TABLE 2

| Screening No. | Microorganism | Concentration Agent | Amount of Concentration Agent (mg/mL) | Percent Capture |
|---|---|---|---|---|
| C-3 | *Salmonella* | Talc | 1 | 63 |
| 3 | *Salmonella* | AS-Talc | 1 | 82 |
| C-4 | *Salmonella* | Talc | 5 | 64 |
| 4 | *Salmonella* | AS-Talc | 5 | 90 |
| C-5 | *Salmonella* | Talc | 10 | 69 |
| 5 | *Salmonella* | AS-Talc | 10 | 95 |

Concentration Agent Screenings 6-8 and Comparative Screenings 6-8

Using the above-described microorganism concentration test method, 10 mg of AS-Talc and Talc were tested separately against different bacterial concentrations of the target microorganism, *Salmonella enterica* subsp.*enterica serovar Typhimurium* (ATCC 35987). The results are shown in Table 3 below.

TABLE 3

| Screening No. | Microorganism | Concentration Agent | Microorganism Concentration (CFU/mL) | Percent Capture ± Standard Deviation |
|---|---|---|---|---|
| C-6 | *Salmonella* | Talc | 10 | 68 ± 9 |
| 6 | *Salmonella* | AS-Talc | 10 | 92 ± 11 |
| C-7 | *Salmonella* | Talc | 100 | 74 ± 3 |
| 7 | *Salmonella* | AS-Talc | 100 | 98 ± 3 |
| C-8 | *Salmonella* | Talc | 1000 | 69 ± 1 |
| 8 | *Salmonella* | AS-Talc | 1000 | 92 ± 1 |

Concentration Agent Screenings 9-11 and Comparative Screenings 9-11

Using the above-described microorganism concentration test method, 10 mg of AS-Talc and Talc were tested separately for bacterial concentration of the target microorganism, *Salmonella enterica* subsp.*enterica serovar Typhimurium* (ATCC 35987) for 5, 10, and 15 minutes of incubation. The results are shown in Table 4 below (standard deviation for all samples less than 10 percent).

TABLE 4

| Screening No. | Microorganism | Concentration Agent | Incubation Time (minutes) | Percent Capture |
|---|---|---|---|---|
| C-9 | *Salmonella* | Talc | 5 | 74 |
| 9 | *Salmonella* | AS-Talc | 5 | 97 |
| C-10 | *Salmonella* | Talc | 10 | 77 |
| 10 | *Salmonella* | AS-Talc | 10 | 96 |
| C-11 | *Salmonella* | Talc | 15 | 75 |
| 11 | *Salmonella* | AS-Talc | 15 | 92 |

Concentration Agent Screening 12 and Comparative Screening 12

Using the above-described microorganism concentration test method, with the exception of the use of Butterfield's Buffer solution instead of adsorption buffer, 10 mg of AS-Talc and Talc were tested separately for yeast concentration of the target microorganism, *Saccharomyces cerevisiae* ($10^2$ CFU/mL; ATCC 201390). The resulting materials were plated on 3M™ Petrifilm™ Yeast and Mold Count Plate culture medium (dry, rehydratable; 3M Company, St. Paul, Minn.) and incubated for 5 days according to the manufacturer's instructions. Isolated yeast colonies were counted manually, and percent capture was calculated as described above. Percent capture was 97 percent for AS-Talc and 82 percent for Talc (standard deviation for all samples less than 10 percent).

Concentration Agent Screenings 13-15

Food samples were purchased from a local grocery store (Cub Foods, St. Paul). Turkey slices and apple juice (11 g) were weighed in sterile glass dishes and added to sterile Stomacher™ polyethylene filter bags (Seward Corp, Norfolk, UK). The food samples were spiked with bacterial cultures at a $10^2$ CFU/mL concentration using an 18-20 hour overnight culture (stock) of *Salmonella enterica* subsp.*enterica serovar Typhimurium* (ATCC 35987). This was followed by the addition of 99 mL of Butterfield's Buffer solution to each spiked sample. The resulting samples were blended for a 2-minute cycle in a Stomacher™ 400 Circulator laboratory blender (Seward Corp. Norfolk, UK). The blended samples were collected in sterile 50 mL centrifuge tubes (BD Falcon™, Becton Dickinson, Franklin Lakes, N.J.) and centrifuged at 2000 revolutions per minute (rpm) for 5 minutes to remove large debris. The resulting supernatants were used as samples for further testing. The pH of the apple juice-based supernatant was adjusted to 7.2 before testing by adding 1N sodium hydroxide (VWR, West Chester, Pa.). Potable water (100 mL) from a drinking fountain was collected in a sterile 250 mL glass bottle (VWR, West Chester, Pa.) and was inoculated with the target microorganism *Salmonella enterica* subsp.*enterica serovar Typhimurium* (ATCC 35987) at $10^2$ CFU/mL, mixed manually end-to-end 5 times, and incubated at room temperature (25° C.) for 15 minutes. This water sample was used for further testing.

Using the above-described microorganism concentration test method, each 1 mL test sample prepared as above was added separately to a test tube containing 10 mg of AS-Talc and tested for bacterial concentration of the target microorganism, *Salmonella enterica* subsp.*enterica serovar Typhimurium* (ATCC 35987). The results are shown in Table 5 below (standard deviation for all samples less than 10 percent).

TABLE 5

| Screening No. | Microorganism | Concentration Agent | Sample | Percent Capture |
|---|---|---|---|---|
| 13 | *Salmonella* | AS-Talc | Apple Juice | 86 |
| 14 | *Salmonella* | AS-Talc | Turkey | 78 |
| 15 | *Salmonella* | AS-Talc | Water | 98 |

Concentration Agent Screenings 16 and 17

AS-Talc was tested for concentration of the target microorganism *Salmonella enterica* subsp.*enterica serovar Typhimurium* (ATCC 35987) from large-volume samples (300 mg AS-Talc per 30 mL sample volume). Potable water (100 mL) from a drinking fountain was collected in a sterile 250 mL glass bottle (VWR, West Chester, Pa.) and inoculated with the target microorganism *Salmonella enterica* subsp.*enterica serovar Typhimurium* (ATCC 35987) at $10^2$ CFU/mL. The resulting inoculated water was mixed manually end-to-end 5 times and incubated at room temperature (25° C.) for 15 minutes. 30 mL samples of the incubated water were added to sterile 50 mL conical polypropylene centrifuge tubes (BD Falcon™, Becton Dickinson, Franklin Lakes, N.J.) containing 300 mg of AS-Talc and were tested by using the above-described microorganism concentration test method. The resulting settled AS-Talc was re-suspended in 30 mL sterile Butterfield's Buffer solution, and 1 mL of the resulting suspension was plated on 3M™ Petrifilm™ Aerobic Count Plates culture medium. Percent capture was 98 percent (standard deviation less than 10 percent).

Whole grape tomatoes (11 g) from a local grocery store (Cub Foods, St. Paul) were placed in a sterile petridish and were inoculated with the target microorganism *Salmonella enterica* subsp.*enterica serovar Typhimurium* (ATCC 35987) at $10^2$ CFU/mL, mixed manually by swirling 5 times, and incubated at room temperature (25° C.) for 5 minutes. The tomatoes were added to sterile Stomacher™ polyethylene filter bags (Seward Corp, Norfolk, UK) containing 99 mL of Butterfield's Buffer solution. The contents of the bags were mixed by swirling for 1 minute. 30 mL samples were added to sterile 50 mL conical polypropylene centrifuge tubes (BD Falcon™, Becton Dickinson, Franklin Lakes, N.J.) containing 300 mg of AS-Talc and tested for bacterial concentration using the above-described microorganism concentration test method. The AS-Talc particles were settled by centrifugation at 2000 rpm for 5 minutes (Eppendorf, Westbury, N.Y.). The settled particles were re-suspended in 30 mL sterile Butterfield's Buffer solution, and 1 mL of the resulting suspension was plated on 3M™ Petrifilm™ Aerobic Count Plates culture medium. Percent capture was 99 percent (standard deviation less than 10 percent).

Concentration Agent Screenings 18 and 19

10 mg of AS-Talc was tested for concentration of the target bacterial endospores *Bacillus atrophaeus* (ATCC 9372) and *Bacillus subtilis* (ATCC 19659). The above-described microorganism concentration test method was utilized with the following modifications: the overnight cultures had $2 \times 10^2$ CFU/mL *Bacillus atrophaeus* and $7 \times 10^2$ CFU/mL *Bacillus subtilis*, respectively; the resulting supernatants were plated undiluted; the settled concentration agent with bound *Bacillus atrophaeus* was resuspended in 1 mL sterile Butterfield's Buffer solution and plated; and the settled concentration agent with bound *Bacillus subtilis* was resuspended in 5 mL sterile Butterfield's Buffer solution and plated (1 mL each). Capture efficiencies were calculated based on counts from the plated supernatants, and the results are shown in Table 6 below (standard deviation for all samples less than 10 percent).

TABLE 6

| Screening No. | Microorganism | Concentration Agent | Percent Capture |
|---|---|---|---|
| 18 | *Bacillus atrophaeus* | AS-Talc | 97 |
| 19 | *Bacillus subtilis* | AS-Talc | 95 |

Concentration Agent Screenings 20 and 21

10 mg of AS-Talc was tested for concentration of the target non-enveloped, bacteria-infecting virus, *Escherichia coli* bacteriophage MS2 (ATCC 15597-B1; which is often used as a surrogate for various human-infecting, non-enveloped enteric viruses). A double layer agar method (described below) was used to assay for capture of the *Escherichia coli* bacteriophage MS2 (ATCC 15597-B1) using *Escherichia coli* bacteria (ATCC 15597) as host.

*Escherichia coli* bacteriophage MS2 stock was diluted ten-fold serially in sterile 1× adsorption buffer (containing 5 mM KCl, 1 mM CaCl$_2$, 0.1 mM MgCl$_2$, and 1 mM K$_2$HPO$_4$) at pH 7.2 to obtain two dilutions with $10^3$ and $10^2$ plaque forming units per milliliter (PFUs/mL), respectively. A 1.0 mL volume of resulting bacteriophage dilution was added to a labeled sterile 5 mL polypropylene tube (BD Falcon™, Becton Dickinson, Franklin Lakes, N.J.) containing 10 mg of concentration agent and mixed on a Thermolyne Maximix Plus™ vortex mixer (Barnstead International, Iowa). The capped tube was incubated at room temperature (25° C.) for 15 minutes on a Thermolyne Vari Mix™ shaker platform (Barnstead International, Iowa). After the incubation, the tube was allowed to stand on the lab bench for 10 minutes to settle the concentration agent. A control sample tube containing 1.0 mL of the bacteriophage dilution without concentration agent was treated in the same manner. The resulting settled concentration agent and supernatant (and the control sample) were then used for analysis.

100 microliters of the supernatant was removed and assayed for bacteriophage using the double layer agar method described below. An additional 800 microliters of supernatant was removed and discarded. One hundred microliters of the settled concentration agent was also assayed for bacteriophage.

Double Layer Agar Method:

A single colony of *Escherichia coli* bacteria (ATCC 15597) was inoculated into 25 mL sterile 3 weight percent tryptic soy broth (Bacto™ Tryptic Soy Broth, Becton Dickinson and Company, Sparks, Md.; prepared according to manufacturer's instructions) and incubated at 37° C. in a shaker incubator (Innova™ 44, New Brunswick Scientific Co., Inc., Edison, N.J.) set at 250 revolutions per minute (rpm) overnight. 750 microliters of this overnight culture was used to inoculate 75 mL sterile 3 weight percent tryptic soy broth. The resulting culture was incubated at 37° C. in the shaker incubator set at 250 rpm to obtain *Escherichia coli* cells in the exponential phase as measured by absorbance at 550 nm (absorbance values 0.3-0.6) using a SpectraMax M5 spectrophotometer (Molecular Devices, Sunnyvale, Calif.). The cells were incubated on ice until used for assay.

One hundred microliters of the above-described bacteriophage test samples were mixed with 75 microliters of the ice-incubated *Escherichia coli* (host bacteria) cells and incubated at room temperature (25° C.) for 5 minutes. The resulting samples were mixed with 5 mL sterile molten top agar (3 weight percent tryptic soy broth, 1.5 weight percent NaCl, 0.6 weight percent agar; prepared that day and maintained in a 48° C. waterbath). The mixture was then poured on top of bottom agar (3 weight percent tryptic soy broth, 1.5 weight percent NaCl, 1.2 weight percent agar) in petridishes. The molten agar component of the mixture was allowed to solidify for 5 minutes, and the petridishes or plates were inverted and incubated at 37° C. The plates were visually inspected after overnight incubation, and those plates containing settled concentration agent (as well as the control plate) showed the presence of bacteriophage plaques. Capture efficiencies were calculated based on counts from the plated supernatants and determined to be 72 percent for the $10^2$ PFU/mL dilution (standard deviation less than 10 percent).

Concentration Agent Screening 22

Apple juice was purchased from a local grocery store (Cub Foods, St. Paul). Apple juice (11 g) was weighed in a sterile glass dish and added to 99 mL sterile Butterfield's Buffer. The resulting combination was mixed by swirling for 1 minute and was spiked with two bacterial cultures, each at a 1 CFU/mL concentration, using 18-20 hour overnight cultures (bacterial stocks) of *Salmonella enterica* subsp.*enterica serovar Typhimurium* (ATCC 35987) and *Escherichia coli* (ATCC 51813). Serial dilutions of the bacterial stocks had been made in 1× adsorption buffer as described above.

Using the above-described microorganism concentration test method, a 10 mL volume of the spiked apple juice sample was added to a sterile 50 mL conical polypropylene centrifuge tube (BD Falcon™, Becton Dickinson, Franklin Lakes, N.J.) containing 100 mg of AS-Talc and incubated for 15 minutes for bacterial capture/concentration of the target microorganism, *Salmonella* (in the presence of the *Escherichia coli*, a competitor microorganism). The resulting supernatant was removed, and the settled concentration agent was transferred to another sterile 50 mL tube containing 2 mL sterile 3 weight percent tryptic soy broth (Bacto™ Tryptic Soy Broth, Becton Dickinson and Company, Sparks, Md.; prepared according to manufacturer's instructions). The tube was loosely capped, and its contents were mixed and incubated at 37° C. After overnight incubation, the resulting broth mixture was tested for the presence of *Salmonella* using a RapidChek™ *Salmonella* lateral flow immunoassay test strip from SDI (Strategic Diagnostics, Inc., Newark, Del.). Visual inspection of the test strip showed it to be positive for *Salmonella*.

Nucleic acid detection by polymerase chain reaction (PCR) was also carried out for the microorganism-containing broth mixture. 1 mL of the above-described overnight-incubated, concentration agent-containing broth was assayed as a test sample for the presence of *Salmonella* by using a TaqMan™ ABI *Salmonella enterica* Detection Kit from Applied Biosystems (Foster City, Calif.). As a control sample, 1 mL of the 18-20 hour overnight culture (stock) of *Salmonella enterica* subsp.*enterica serovar Typhimurium* (ATCC 35987) was also assayed. PCR testing was conducted in a Stratagene Mx3005P™ QPCR (quantitative PCR) System (Stratagene Corporation, La Jolla, Calif.) by using the following cycle conditions per cycle for 45 cycles: 25° C. for 30 seconds, 95° C. for 10 minutes, 95° C. for 15 seconds, and 60° C. for 1 minute. An average (n=2) cycle threshold value (CT value) of 17.71 was obtained for the control sample. An average (n=2) CT value of 19.88 was obtained for the test sample containing concentration agent, indicating a positive PCR reaction and confirming the presence of *Salmonella.*

Preparation of Concentration Devices

Two different ultra high molecular weight polyethylene (UHMWPE) powders were obtained from Ticona (a division of Celanese headquartered in Frankfurt, Germany) as PMX1 (product number GUR™ 2126, irregularly shaped, size range of 50-100 micrometers) and PMX2 (product number GUR™ 4150-3, spherical, median particle size of about 40 micrometers). The powders were combined in a 4:1 ratio of PMX1:PMX2. The resulting combination (hereinafter, UHMWPE mixture) was used to prepare two types of concentration devices.

For Concentration Device Type A, a mixture of 40 percent by weight AS-Talc concentration agent (described above) was combined with 60 weight percent of the UHMWPE mixture. For Concentration Device Type B (Control), the UHMWPE mixture was used without added concentration agent. For each concentration device, the selected components were weighed out into a one-liter cylindrical container or jar. The jar was then shaken vigorously for several minutes or, alternatively, placed on a rollermill spinning at a low speed (about 10-15 revolutions per minute (rpm)) for at least two hours, to produce a homogenous blend or floc.

A portion (about 6-10 g) of the floc was then used to fill a 50 mm diameter cylindrical mold, which had a depth of 5 mm and also had 0.05 mm (2 mil) thick disks of polytetrafluoroethylene-impregnated fiberglass placed in its bottom and in its lid to prevent sticking of the floc and to retard heat transfer through the faces of the mold. The floc was compressed into the mold, and the lid of the mold was then pressed into position to close the mold.

The filled mold was placed on a vortex mixer (IKA™ MS3 Digital Vortexer, available from VWR Scientific, West Chester, Pa.) for 10-20 seconds to eliminate voids and cracks in its contents. The mold was then placed in a vented convection oven (Thelco Precision Model 6555 or Thermo-Electron Precision Model 6566, available from Thermo Fisher Scientific, Inc., Waltham, Mass.) set at 175-185° C. for one hour to sinter the floc. After cooling to room temperature (about 23° C.), the resulting sintered floc was removed from the mold and, if larger than 47 mm in diameter, trimmed using a punch die to a 47 mm diameter for use as a concentration device.

EXAMPLE 1

An isolated bacterial colony of *Salmonella enterica* subsp.*enterica serovar Typhimurium* (ATCC 35987) was inoculated into 5 mL BBL™ Trypticase™ Soy Broth (Becton Dickinson, Sparks, Md.) and incubated at 37° C. for 18-20 hours. This overnight culture at a concentration of about $1\times10^9$ CFU/mL was diluted in Butterfield's Buffer (pH 7.2±0.2; monobasic potassium phosphate buffer solution; VWR Catalog Number 83008-093, VWR, West Chester, Pa.) to obtain an approximately $1\times10^3$ CFU/mL inoculum.

A volume of 250 mL potable water (from a drinking fountain) was spiked with a 1:100 dilution of the approximately $1\times10^3$ CFU/mL inoculum, resulting in a sample having a concentration of about 11 CFU/mL (total of about 2600 CFUs in the approximately 250 mL sample). The sample was pumped through a Type A (As-Talc) concentration device (prepared essentially as described above) at a flow rate of 10 mL/minute for 25 minutes using a custom made sample holder for the concentration device (the holder consisting of upper and lower flow distribution plates with a plastic tube machined out to provide a friction fit for the 47 mm diameter concentration device; O-rings were used to prevent leakage on the upstream and downstream sides; throughbolts provided closure pressure), a peristaltic pump (Heidolph™ Pump Drive 5201, available from VWR Scientific, West Chester, Pa.), and 3.1 mm internal diameter tubing. A digital pressure sensor (SSI Technologies Model MGI-30-A-9V, Cole-Parmer, Vernon Hills, Ill.) was placed upstream of the sample holder to monitor pressure drop.

Flow through sample fractions (1 mL) were collected in labeled sterile 5 mL polypropylene tubes (BD Falcon™, Becton Dickinson, Franklin Lakes, N.J.) every five minutes for 25 minutes and were plated onto 3M™ Petrifilm™ Aerobic Count Plates culture medium (dry, rehydratable; 3M Company, St. Paul, Minn.) according to the manufacturer's instructions. After the sample was passed through the concentration device, the concentration device was 'flushed' with filter-sterilized 20 mL Butterfield's Buffer containing 500 micrograms/mL BSA (Bovine Serum Albumin, stock of 1 mg/mL in water, powder purchased from Sigma Chemicals, St Louis. Mo) for elution of bacteria by reversing the flow (5 mL/min). The resulting eluate was collected in a sterile 50 mL polypropylene tube and plated essentially as described above.

After the flushing, the concentration device was removed from its holder using sterile forceps and was incubated overnight in a sterile Stomacher™ polyethylene filter bag (PE-LD Model 400, Seward Corp, Norfolk, UK) containing 100 mL of sterile 3 weight percent tryptic soy broth (Bacto™ Tryptic Soy Broth, Becton Dickinson, Sparks, Md., prepared according to manufacturer's instructions). The bag was loosely tied and incubated at 37° C. for 18-20 hours, along with the plated flow through sample fractions and the plated eluate. The incubated plates were quantified the next day according to the manufacturer's instructions.

Capture efficiency was calculated based on counts obtained from the plated flow through sample fractions by using the formula below (where CFU=Colony Forming Unit, which is a unit of live or viable microorganisms):

Percent CFUs in Fraction=(number of colonies from plated fraction)/(total number of colonies in sample)×100

Capture Efficiency or Percent Capture=100−Percent CFUs in Fraction

A capture efficiency of greater than 99 percent was obtained. Elution (by reversing the flow) released approximately 25 percent (660/2600 CFUs) of the captured inoculum.

The overnight cultured broth containing the concentration device was tested for the presence of *Salmonella* using a SDI RapidChek® *Salmonella* lateral flow immunoassay strip from SDI (Strategic Diagnostics Inc., Newark, Del.), and a positive result was obtained. The overnight cultured broth containing the concentration device was diluted in Butterfield's Buffer and plated onto 3M™ Petrifilm™ Aerobic Count Plates (3M Company, St. Paul, Minn.), which were incubated at 37° C. for 18-20 hours and quantified the next day. Plate counts indicated that the captured *Salmonella* in the concentration device had increased in number to a concentration of about $2 \times 10^9$ CFU/mL.

COMPARATIVE EXAMPLE 1

The procedure of Example 1 was essentially repeated using a Type B (control) concentration device (no concentration agent) instead of the Type A (As-Talc) concentration device, and using a spiked potable water sample having about 13 CFU/mL (total of about 3300 CFUs in the approximately 250 mL sample). A capture efficiency of greater than 99 percent was obtained, and elution (by reversing the flow) released approximately 2.4 percent (80/3300 CFUs) of the captured inoculum (an order of magnitude less than the percent eluted in Example 1 above). This elution result suggests that a concentration device of the invention can provide advantages over the comparative device in the isolation or separation of captured microorganisms to facilitate further analysis.

EXAMPLES 2 AND 3 AND COMPARATIVE EXAMPLE 2

An overnight streaked culture of *Listeria innocua* (ATCC 33090) from a blood agar plate (Tryptic Soy Agar with 5 weight percent sheep blood, Hardy Diagnostics, Santa Maria, Calif.) that had been incubated for 18 hours at 30° C. was used to make a 0.5 McFarland Standard (using a DensiCHEK™ densitometer, bioMerieux, Inc., Durham, N.C.) in 3 mL Butterfield's Buffer (pH 7.2±0.2; monobasic potassium phosphate buffer solution; VWR Catalog Number 83008-093, VWR, West Chester, Pa.). The resulting bacterial stock containing $1 \times 10^8$ CFUs/mL was serially diluted in Butterfield's Buffer to obtain an approximately $1 \times 10^3$ CFUs/mL inoculum.

Bagged iceberg lettuce (Example 2) and organic spinach (Example 3) were purchased from a local grocery store (Cub Foods, St. Paul, Minn.). 25 grams of the lettuce and of the spinach (hereinafter, produce samples) were weighed separately in sterile Stomacher™ polyethylene filter bags (Seward Corp, Norfolk, UK). A 1:1000 dilution of the approximately $1 \times 10^3$ CFUs/mL inoculum was inoculated onto the produce samples to obtain a final concentration of 1 CFU/mL in each produce sample. Each inoculated produce sample was mixed by shaking the bags for 30 seconds, and this was followed by a 10-minute incubation period at room temperature (23° C.) to allow attachment of the bacteria to the produce.

A volume of 225 mL Butterfield's Buffer (pH 7.2±0.2; monobasic potassium phosphate buffer solution; VWR Catalog Number 83008-093, VWR, West Chester, Pa.) was added to each incubated produce sample, resulting in a sample having a concentration of about 1 CFU/mL (total of about 250 CFUs in the approximately 250 mL produce sample). The resulting produce samples were blended for a 1-minute cycle at 200 revolutions per minute (rpm) in a Stomacher™ 400 Circulator laboratory blender (Seward Corporation, Norfolk, UK). The blended produce samples were removed from the bags by pipetting and were collected in separate sterile 250 mL glass bottles (VWR, West Chester, Pa.).

The collected produce samples were each pumped through a Type A (As-Talc) concentration device (the two devices were prepared essentially as described above) at a flow rate of 10 mL/minute for 25 minutes, using the above-described (in Example 1) custom made sample holder for the concentration device, a peristaltic pump (Heidolph™ Pump Drive 5201, available from VWR Scientific, West Chester, Pa.), and 3.1 mm internal diameter tubing.

The entire 250 mL lettuce sample was passed through the concentration device. Flow-through fractions (1 mL) from the lettuce sample were collected in labeled, sterile 5 mL polypropylene tubes (BD Falcon™, Becton Dickinson, Franklin Lakes, N.J.) every five minutes for 25 minutes and were spread plated (100 microliters) onto Modified Oxford Medium plates (Hardy Diagnostics, Santa Maria, Calif.). The plates were inverted and incubated at 37° C. for 18-20 hours.

Flow-through fractions (1 mL) from the spinach sample were collected in labeled, sterile 5 mL polypropylene tubes (BD Falcon™, Becton Dickinson, Franklin Lakes, N.J.) every five minutes for 15 minutes and were plated onto Modified Oxford Medium plates (Hardy Diagnostics, Santa Maria, Calif.) and processed similarly. The pumping was terminated after 15 minutes when the flow stopped, presumably due to clogging of the concentration device. Only half of the 250 mL spinach sample was processed through the concentration device.

A 100 microliter volume from a 1:10 dilution of the $1 \times 10^3$ CFUs/mL inoculum was plated similarly as an inoculum control (no concentration).

After the produce samples were passed through the concentration devices, the concentration device was removed from its holder using sterile spatulas and was placed into a sterile polypropylene culture dish (60 mm×15 mm, Corning polypropylene culture dishes, available from VWR, West Chester, Pa., catalog #25382-381) containing 5 mL of sterile 3.7 weight percent brain heart infusion broth (BBL™ Brain Heart Infusion Broth, Becton Dickinson, Sparks, Md., prepared according to manufacturer's instructions) and incubated at 37° C. for 18-20 hours.

For comparison (as Comparative Example 2), a blended spinach sample spiked with *Listeria innocua* (prepared essentially as described above, 25 grams blended in 225 ml Butterfield's Buffer) was processed thru a sterile 47 mm diameter, 0.45 micron pore size, mixed cellulose esters membrane filter (catalog #HAWP04700, Millipore Corporation, Bedford, Mass.) by vacuum filtration. A volume of about 8 mL of the 250 mL sample was processed before the flow stopped, presumably due to clogging of the filter. The processing was terminated.

The incubated Modified Oxford Medium plates were quantified the next day by manual counting. Capture efficiency was calculated based on counts obtained from the plated flow-through sample fractions by using the formula below (where CFU=Colony Forming Unit, which is a unit of live or viable microorganisms):

Percent CFUs in Fraction=(number of colonies from plated fraction)/(total number of colonies in sample)×100

Capture Efficiency or Percent Capture=100−Percent CFUs in Fraction

A capture efficiency of greater than 99 percent was obtained for the device used for concentrating the lettuce sample. No bacterial colonies were observed in the 5 minute, 10 minute, and 15 minute flow-through fractions of the spinach sample. Based on colony counts, the spiked lettuce and spinach samples each contained a total of 500 CFUs.

Each overnight cultured broth containing the concentration device was tested for the presence of *Listeria* using a 3M™ Tecra™ *Listeria* Visual Immunoassay kit from 3M (available from 3M Australia Pty Ltd., Frenchs Forest, Australia) according to the manufacturer's instructions. A positive result was obtained for both the lettuce and spinach samples (absorbance value at 414 nanometers of each sample, tested in duplicate, was greater than 0.2, and of the negative control was less than 0.2 (actual absorbance value of 0.055)).

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A concentration device comprising a sintered porous polymer matrix comprising at least one concentration agent that comprises an amorphous metal silicate and that has a surface composition having a metal atom to silicon atom ratio of less than or equal to 0.5, as determined by X-ray photoelectron spectroscopy (XPS), wherein about 75 to about 99 volume percent of the amorphous metal silicate is free of sharp corners or edges, wherein said metal is magnesium.

2. The concentration device of claim 1, wherein said sintered porous polymer matrix comprises at least one thermoplastic polymer.

3. The concentration device of claim 2, wherein said thermoplastic polymer is selected from olefin homopolymers, olefin copolymers, copolymers of olefins and other vinyl monomers, and combinations thereof.

4. The concentration device of claim 3, wherein said thermoplastic polymer is selected from olefin homopolymers and combinations thereof.

5. The concentration device of claim 4, wherein said olefin homopolymer is polyethylene.

6. The concentration device of claim 5, wherein said polyethylene comprises an ultra-high molecular weight polyethylene having a molecular weight of at least about 750,000.

7. The concentration device of claim 1, wherein said sintered porous polymer matrix comprises at least one polymer having a particle shape comprising surface convolutions.

8. The concentration device of claim 1, wherein said concentration device comprises a tortuous path matrix.

9. The concentration device of claim 1, wherein said surface composition has a metal atom to silicon atom ratio of less than or equal to 0.4.

10. The concentration device of claim 1, wherein said surface composition has a metal atom to silicon atom ratio of less than or equal to 0.3.

11. The concentration device of claim 1, wherein said concentration agent has a negative zeta potential at a pH of 7.

12. The concentration device of claim 1, wherein said concentration agent has a zeta potential in the range of about −9 millivolts to about −25 millivolts at a pH of 7.

13. The concentration device of claim 1, wherein said concentration agent comprises an amorphous metal silicate in at least partially fused particulate form and having a particle size in the range of 1 micrometer to 15 micrometers.

14. The concentration device of claim 13, wherein said concentration agent is amorphous, spheroidized magnesium silicate.

15. The concentration device of claim 1, wherein said concentration agent is present in an amount of up to about 90 weight percent of the concentration device.

16. The concentration device of claim 1, wherein said concentration agent is present in an amount of between about 10 weight percent and about 80 weight percent of the concentration device.

17. The concentration device of claim 1, wherein said concentration agent comprises at least one particulate concentration agent embedded in or on the surface of the porous polymer matrix.

18. The concentration device of claim 1, wherein said concentration agent is shaped as solid spheres.

19. The concentration device of claim 7, wherein said at least one polymer having a particle shape comprising surface convolutions has a bulk density of 0.25-0.30 grams per cubic centimeter.

20. The concentration device of claim 1, wherein the concentration agent has a surface area of 3.3 $m^2/g$, a particle density of 2.3 g/cc, or both.

* * * * *